(12) United States Patent
Yang et al.

(10) Patent No.: US 6,611,339 B1
(45) Date of Patent: Aug. 26, 2003

(54) PHASE DISPERSIVE TOMOGRAPHY

(75) Inventors: Changhuei Yang, Cambridge, MA (US); Adam Wax, Boston, MA (US); Michael S. Feld, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 19 days.

(21) Appl. No.: 09/591,297

(22) Filed: Jun. 9, 2000

(51) Int. Cl.$^7$ ................................................ G01B 9/02

(52) U.S. Cl. .................................. 356/485; 356/479

(58) Field of Search ................... 356/496, 497, 356/479, 489

(56) References Cited

U.S. PATENT DOCUMENTS

| | | | |
|---|---|---|---|
| 4,948,254 A | 8/1990 | Ishida | |
| 5,303,026 A | 4/1994 | Strobl et al. | |
| 5,394,240 A | 2/1995 | Matsumoto | |
| 5,416,582 A | 5/1995 | Knutson et al. | |
| 5,424,843 A | 6/1995 | Tromberg et al. | |
| 5,459,570 A | * 10/1995 | Swanson et al. | 356/479 |
| 5,528,365 A | 6/1996 | Gonatas | |
| 5,713,352 A | 2/1998 | Essenpreis et al. | |
| 5,772,587 A | 6/1998 | Gratton et al. | |
| 5,919,140 A | 7/1999 | Perelman et al. | |
| 5,931,789 A | 8/1999 | Alfano et al. | |
| 5,936,739 A | 8/1999 | Cameron et al. | |
| 5,994,690 A | 11/1999 | Kulkarni et al. | |
| 6,002,480 A | 12/1999 | Izatt et al. | |

FOREIGN PATENT DOCUMENTS

WO    WO 01/84124    11/2001

OTHER PUBLICATIONS

Irby, J. et al. "A two-color interferometer using a frequency doubled diode pumped laser for electron density measurements," Review of Scientific instruments, 70 (1): 699–702, (1999).*

Barbour, R.L., et al., "Imaging of Subsurface Regions of Random Media by Remote Sensing" SPIE Time–Resolved Spectroscopy and Imaging of Tissues 1431:192–203, (1991).

Barbour, R.L., et al., "Imaging of Diffusing Media by a Progressive Iterative Backprojection Method Using Time–Domain Data" SPIE 1641:21–34, (1992).

Chernomordik, V., et al., "Point Spread Functions of Photons in Time–Resolved Transillumination Experiments Using Simple Scaling Arguments", Med. Phys. 23(11): 1857–1861, Nov. 1996.

Colak, S.B., et al., "Tomographic Image Reconstruction from Optical Projections in Light–Diffusing Media" Applied Optics, 36(1):180–231 (Jan. 1997).

(List continued on next page.)

*Primary Examiner*—Samuel A. Turner
*Assistant Examiner*—Patrick Connolly
(74) *Attorney, Agent, or Firm*—Bowditch & Dewey, LLP

(57) ABSTRACT

Radiation that propagates undeflected through a turbid medium, undergoes a small change in phase velocity due to its wave nature. This change can be measured using a differential phase optical interferometer. Ballistic propagation can be classified into three regimes: For scatterers small compared to the wavelength, the turbid medium acts as a bulk medium; for large scatterers, phase velocity is independent of turbidity; and in the intermediate regime the phase velocity is strongly dependent on scatterer radius. In particular, for scatterers having intermediate size a phase velocity increase and negative dispersion is observed by adding positive dispersion scatterers of higher refractive index. These measurements are made using the phase difference between fundamental and harmonic light and can be used to provide diagnostic information and images of tissue or biological fluids.

40 Claims, 7 Drawing Sheets-

OTHER PUBLICATIONS

Winn, J.N., et al., "Distribution of the Paths of Early–Arriving Photons Traversing a Turbid Medium" *Applied Optics,* 37(34):8085–8091 (Dec. 1, 1998).

Ueda, Y., "Average Value Method: A New Approach to Practical Optical Computed Tomography for a Turbid Medium Such as Human Tissue" *Jpn. J. Appl. Phys.* 37(Part 1)(5A):21717–2723 (May 1998).

Hebden, J.C., et al., "Simultaneous Reconstruction of Absorption and Scattering Images by Multichannel Measurement of Purely Temporal Data" *Optics Letters* 24(8):534–536 (Apr. 15, 1999).

Eda, H., et al., "Multichannel Time–Resolved Optical Tomographic Imaging System" *Review of Scientific Instruments* 70(9): 3595–3602 (Sep. 1999).

Zanios, G., et al., "Diffuse Reflectance Spectroscopy of Human Adenomatous Colon Polyps In Vivo" *Applied Optics, in press* 1–38 (1999).

Irby, J., et al., "A Two–color Interferometer Using a Frequency Doubled Diode Pumped Laser for Electron Density Measurements" *Review of Scientific Instruments* 70(1):699–702 (Jan. 1999).

Chen, K. et al., "Optical Computed Tomography in a Turbid Medium using Early Arriving Photons" *Journal of Biomedical Optics* 5(2):144–154 (Apr. 2000).

Yang, C., et al., "Feasibility of Field–Based Light Scattering Spectroscopy" *Journal of Biomedical optics, Millennium Issue* 1–22(2000).

Yang, C., et al., "Phase–dispersion optical tomography," *Optics Letters* 26(10):686–688.

Yang, C., et al., "Measurement of the Anomalous Phase Velocity of Ballistic Light in a Random Medium by Use of a Novel Interferometer," *Optics Letters* 26(4):235–237 (Feb. 2001).

Yang, C., et al., "Interferometric phase–dispersion microscopy," *Optics Letters* 25(20):1526–1528 (Oct. 2000).

Irby, J., et al., "A two–color interferometer using a frequency doubled diode pumped laser for electron density measurements," *Review of Scientific Instruments, 70* (1): 699–702, (1999).

* cited by examiner

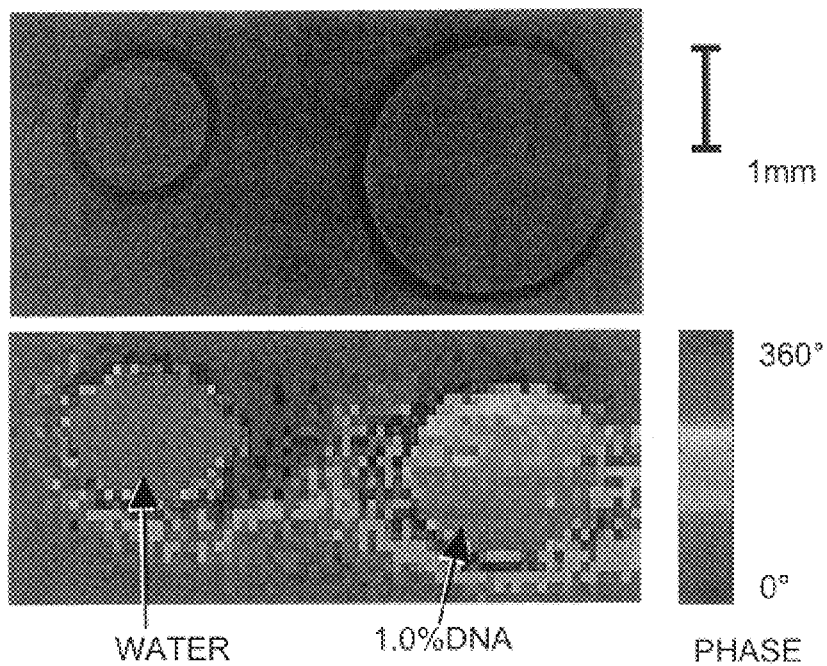
Figure 5A
Figure 5B
WATER    1.0%DNA    PHASE
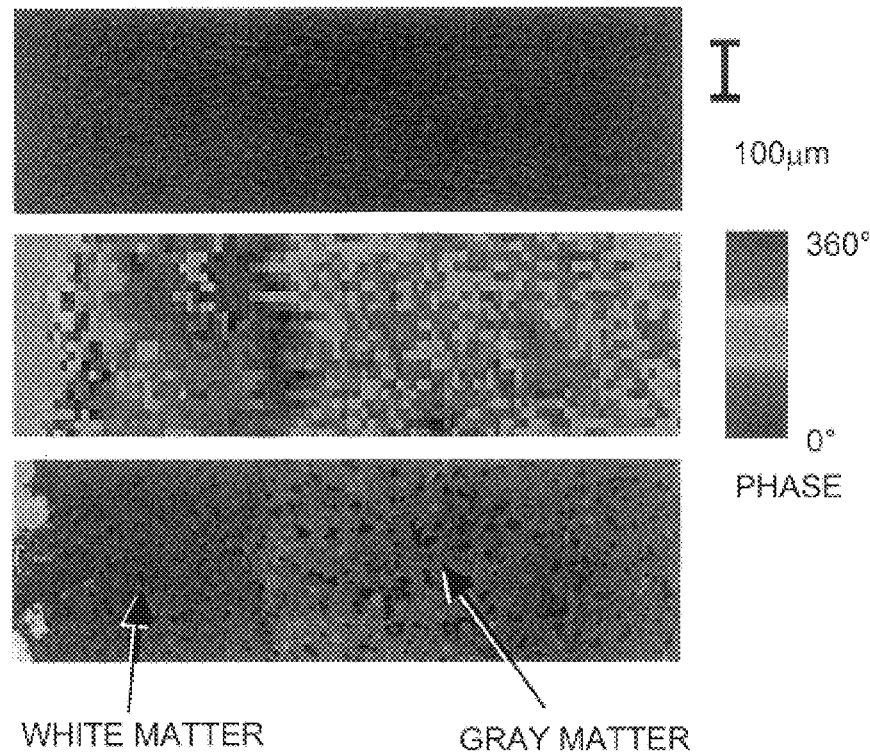
Figure 6A-1
Figure 6A-2
Figure 6A-3
WHITE MATTER    GRAY MATTER

PHASE DISPERSIVE TOMOGRAPHY

GOVERNMENT SUPPORT

The invention was supported, in whole or in part, by Grant Nos. P41-RR02594, 1 F32 RR05075-01 and 1F32 CA80345-01 from the National Institutes for Health and by Grant No. 9708265CHE of the National Science Foundation. The Government has certain rights in the invention.

BACKGROUND OF THE INVENTION

Ballistic light is defined as the light which traverses a scattering medium in the same direction as the incident light. Conventionally, ballistic propagation is pictured as photons which are undeflected in transmission. Such a picture, henceforth called the photonic model, is extensively used in optical tomography, and it explains many properties of ballistic propagation. For example, the photonic model explains the emergence of ballistic light from a thick turbid medium at an earlier time than the scattered light. However, this model is incomplete, as the wave nature of the light is not considered.

Interferometers have been used to measure phase changes based on fluctuations in path length. Phase measurements using interference microscopes, for example, have been used previously to provide two dimensional images of thin tissue samples.

However, there is a continuing need for improvements in systems and methods for measuring turbid media such as tissue.

SUMMARY OF THE INVENTION

The phase velocity of light traversing a diffuse scattering medium is a function of scatterer size. To measure this effect optically, an interferometer that measures very small differences in phase velocity between at least two harmonically related wavelengths is used, such as 800 and 400 nm, for example. One wavelength that is an integer multiple of the other wavelength can thus be used to provide quantitative phase information regarding a scanned region of interest. A pair of such wavelengths can be generated harmonically or by using two separate light sources which satisfy the integer multiple requirement to within 5% of the lowest wavelength, i.e. one wavelength is about an integer multiple of the other wavelength. In a preferred embodiment, the interferometer system of the present invention is sensitive to phase velocity differences at least of 40 m/s in a 2 cm thick turbid sample, for example, or equivalently an optical path length difference of about 5 nm. This sensitivity provides for the measurement of very dilute turbid media, a more relevant model for optical applications such as biomedical imaging and remote sensing through atmospheric conditions such as smoke or fog.

The variations in phase velocity result from the wave nature of ballistic propagation and can be measured by treating the ballistic electromagnetic field as the interference of the input light field with the scattered field. Using van de Hulst and Mie scattering theories, ballistic propagation separates into three regimes: (1) When the scatterer size ($\alpha$) is much smaller than the optical wavelength ($\lambda$), the turbid medium may be approximated as a bulk medium for phase velocity considerations; (2) when a is comparable to $\lambda$, the phase velocity is strongly dependent on scatterer size; (3) when $\alpha$ is much larger than $\lambda$, turbidity can be ignored for phase velocity considerations. Consequently, by measuring tissue with appropriate harmonically related wavelengths of light, the size and distribution of cellular structures within the tissue can be measured.

Ballistic light can propagate with a phase velocity that is uncharacteristic of the constituent materials of the turbid medium. Hence, the ballistic light itself must carry phase information about the structure and composition of the turbid medium. The photonic model simply cannot explain this variation in phase velocity.

A preferred embodiment of the invention relates to a microscopy imaging system referred to herein as phase dispersion microscopy (PDM). This system is based on measuring the phase difference between a fundamental wavelength of light and a harmonic of unscattered light that are transmitted through a medium. PDM employs an interferometer that substantially reduces or eliminates noise due to optical path length fluctuations. In other phase measurement techniques, it is difficult to account for minute interferometer path length differences in the measured phase. Thus, without an independent way of eliminating such jitter, phase measurements cannot directly yield physically relevant information. In contrast, the phase measured in the present system is independent of path length errors. As an example, the system is used to measure very small anomalous phase velocity differences experienced by ballistic light during propagation through turbid media. The present system and method can provide quantitative information by measuring the refractive index dispersion of very dilute material such as DNA-water solutions. The sensitivity of the technique and its image formation capabilities can be applied of the imaging of an unsustained tissue section.

This technique can be used to provide two dimensional (2D) or three dimensional (3D) imaging of tissue both in vitro and in vivo. Additional details regarding the systems and methods of the invention can be found in Application Ser. No. 60/200,187 filed on Apr. 28, 2000 which is incorporated herein by reference.

BRIEF DESCRIPTION OF THE DRAWINGS

The file of this patent contains at least one drawing executed in color. Copies of this patent with color drawings will be provided by the Patent and Trademark Office upon request and payment of the necessary fee.

versus normalized scatter size, $\rho$ where the normalized refractive index difference, (m−1), equals 0.2 for this particular example.

Figure 4:
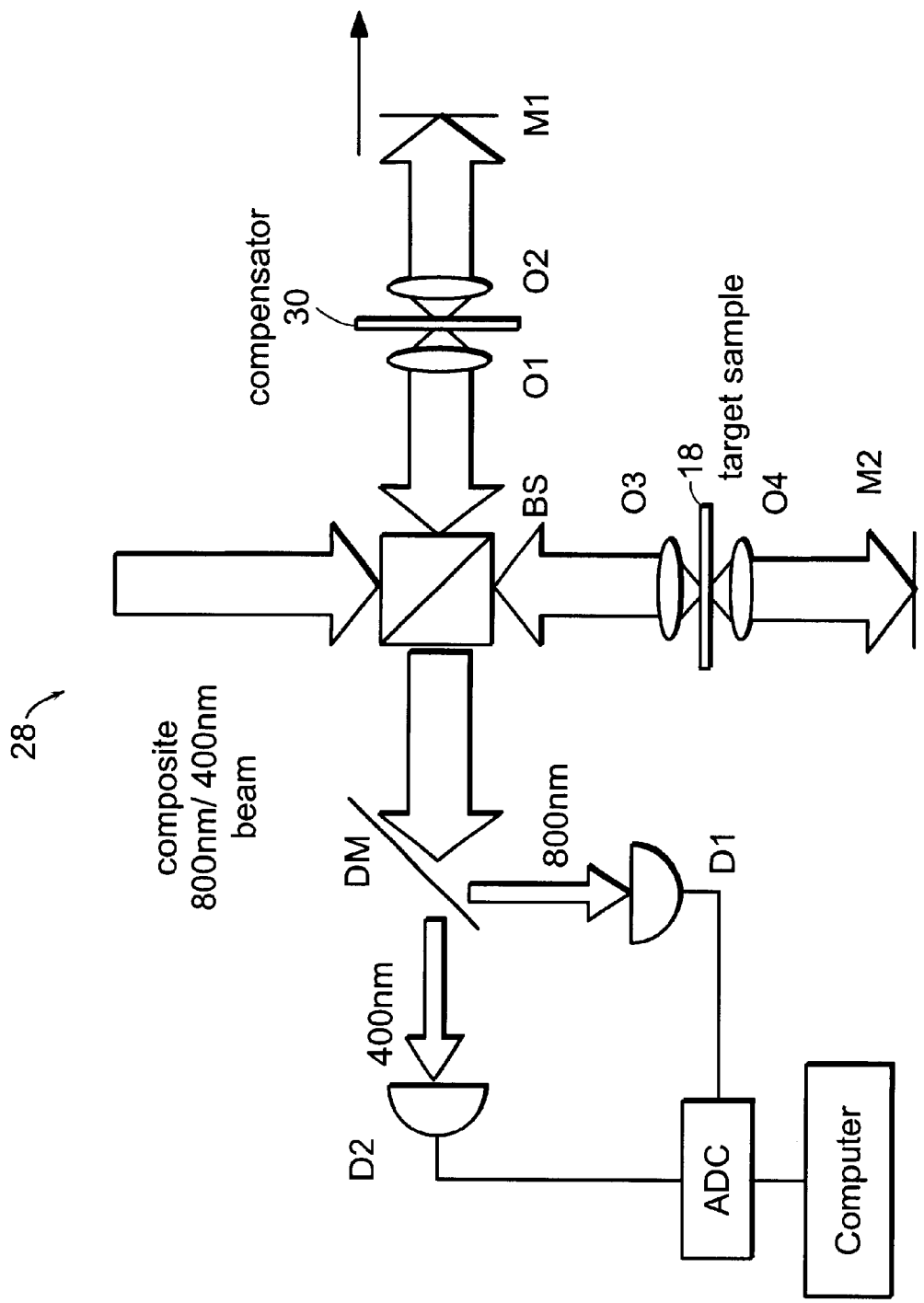

FIG. 4 is another preferred embodiment of the invention using mirrors, M1 and M2, a beamsplitter BS, microscopic objective lens O1, O2, O3 and O4, photodetectors D1 and D2, and a 400 nm/ 800 nm dichroic mirror DM.

FIGS. 5A and 5B, hereinafter collectively referred to as FIG. 5, compare images from a phase contrast system (top) and PDM (bottom) of a drop of water and a drop of 1.0% DNA solution sandwiched between 2 cover slips in which the measured refractive index dispersion, ($\Delta n_{400nm} - \Delta n_{800nm}$), of the DNA solution was $(1.3\pm0.2)\times10^{-4}$.

Figure 1:
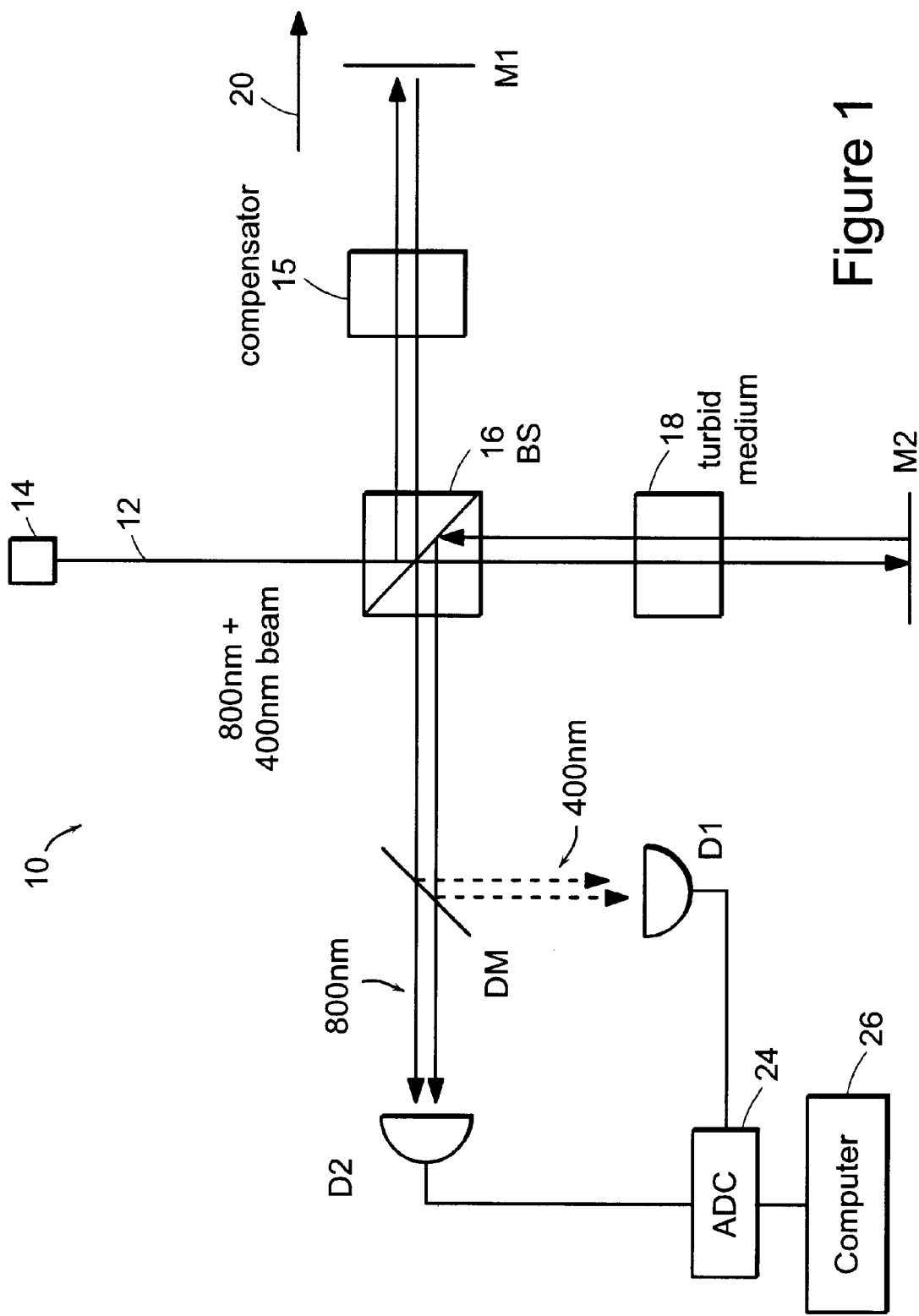
FIG. 1 illustrates a phase measurement system in accordance with the invention including mirrors. M1 and M2 are beamsplitters BS, D1 and D2 are photodetectors, and DM is a 400 nm/800 nm dichroic mirror.
Figure 3:
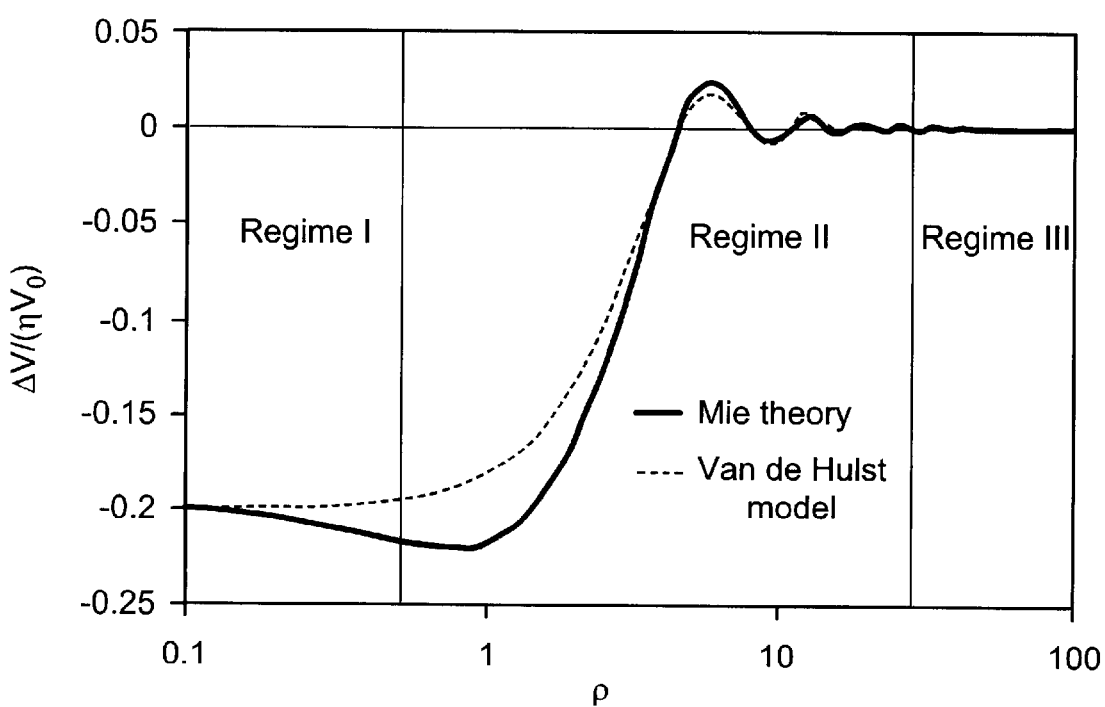
FIG. 3 graphically illustrates a representation of modeled normalized phase velocity, $$\frac{\Delta v}{\eta v_0}$$

FIGS. 6A-1–6A-3, hereinafter collectively referred to as FIG. 6A, include images of a white matter-gray matter interface in a 16 μm thick brain sample with the top being a phase contrast image, the middle being a phase dispersion image in accordance with the present invention and the bottom image being an adjacent frozen section stained with hemotoxylin and eosin.

Figures 1, 6B:
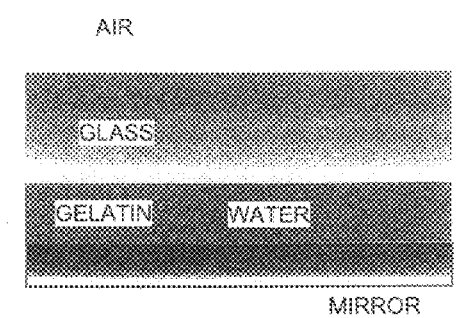
Figures 2, 6B:
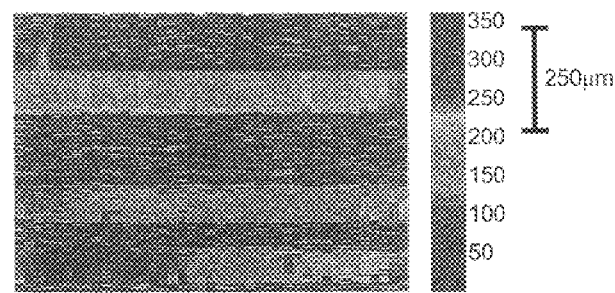
Figures 3, 6B:
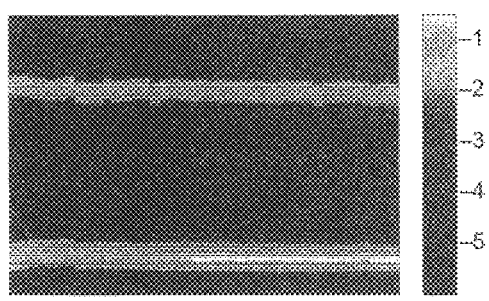
Figures 4, 6B:
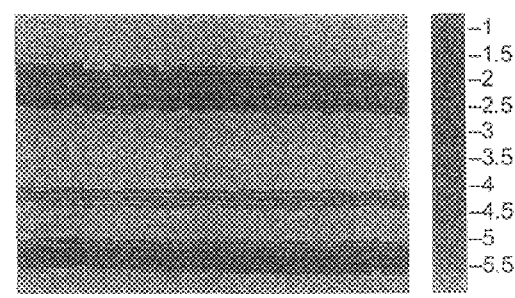

FIGS. 6B-1–6B-4, hereinafter collectively referred to as FIG. 6B, compare the 3D imaging of the present invention with standard OCT images.

Figure 7:
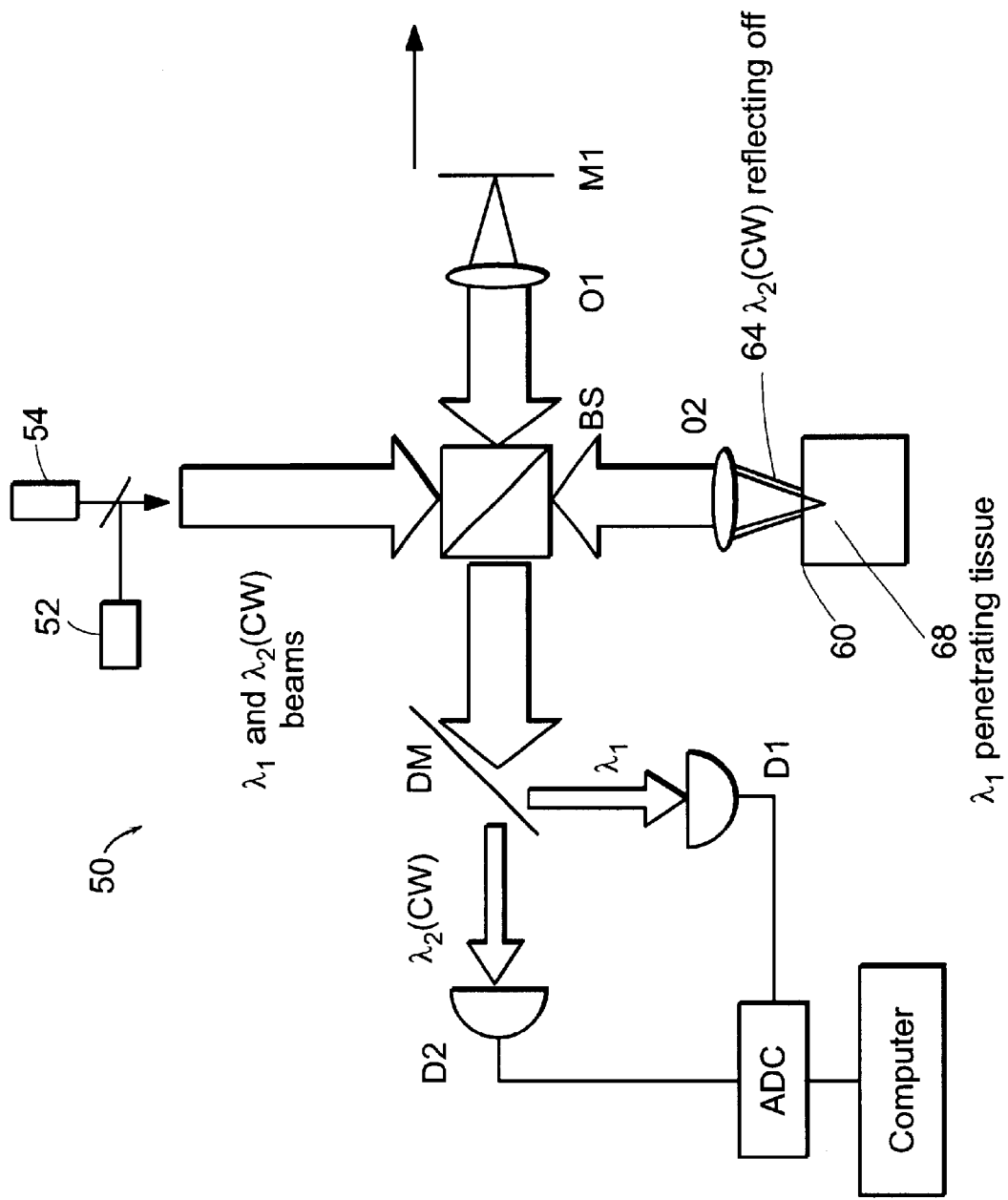

FIG. 7 illustrates systems used for imaging of tissue in accordance with the invention.

Figure 8:
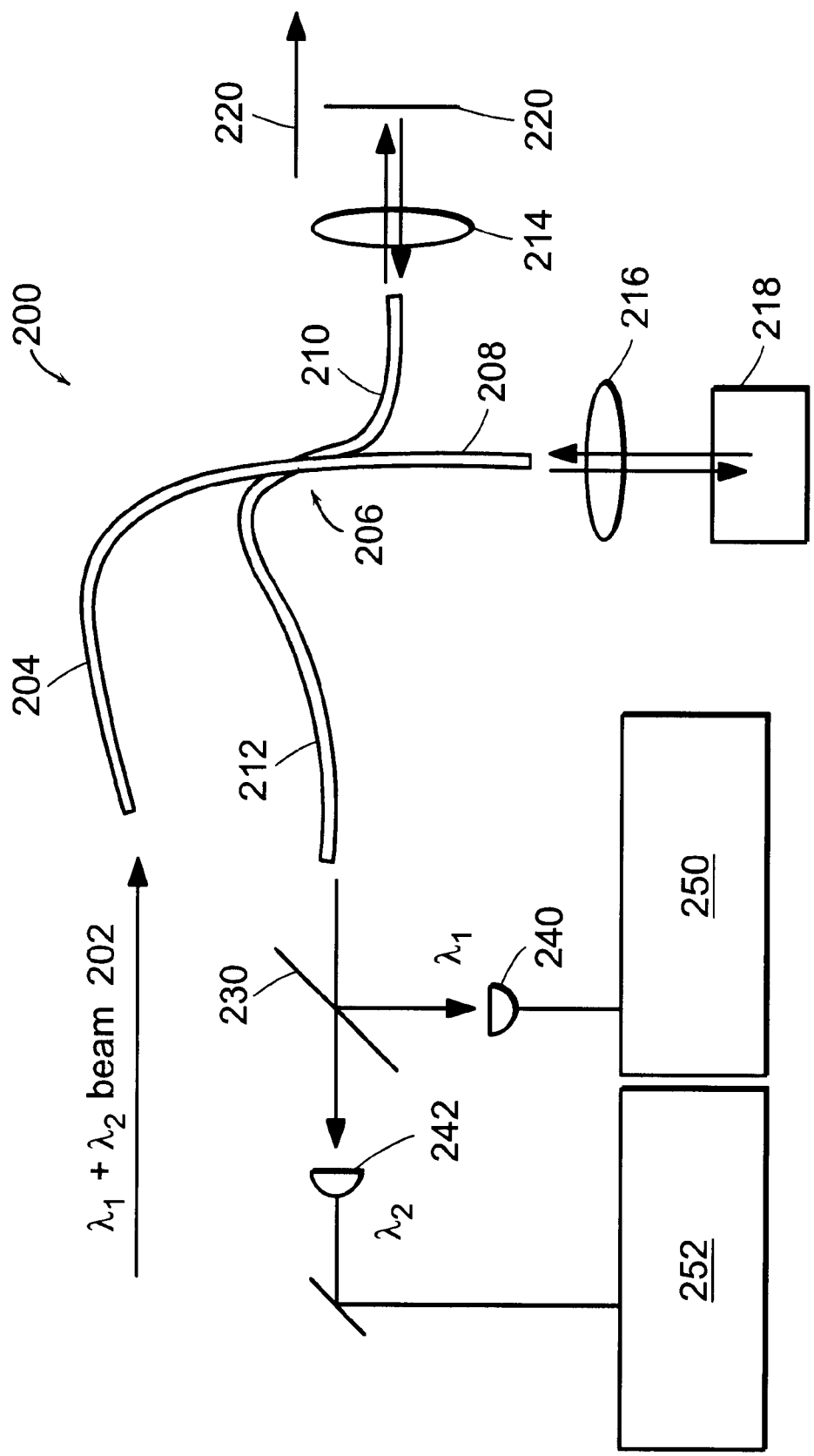

FIG. 8 illustrates the use of a fiber optic system in accordance with the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The measurements are made using a low-coherence phase dispersion interferometer 10 shown in FIG. 1. The input light 12 is created by superposing beams of laser light at the fundamental and preferably the second harmonic frequencies. The source 14 can be a low coherence Ti:sapphire laser producing 150 fs pulses at 800 nm, and the second harmonic is generated by a standard frequency doubler. The superposed beam is split into two components at the beamsplitter 16. One component makes two passes through the turbid medium 18 in the signal arm of the interferometer with mirror M2. The other component passes through a compensator cuvette of water 15 and reflects from a reference mirror M1 in the reference arm. The reference mirror M1 moves at a constant velocity 20 and induces a Doppler shift on the return beam. The recombined beams are then separated by wavelength using a dichroic mirror DM and measured separately by photodetectors D1 and D2. The resulting heterodyne signals at both wavelengths are measured and digitized by a 16-bit 100 kHz A/D converter 24 and further processed and stored in memory with data processor 26. Each digitized signal is bandpassed around its center heterodyne frequency, given by the Doppler shift. The filtered signals are then Hilbert transformed, and the respective phases $\Psi_1$ (fundamental) and $\Psi_2$ (second harmonic) are extracted. Related phase techniques have been used to measure the dispersion of metals and the refractive index of air.

In a conventional interferometer, path length fluctuations as small as a tiny fraction of a wavelength will vary the measured phase significantly; therefore, without an independent way of eliminating such jitter, phase measurements cannot directly yield physically relevant information. However, it can be seen that jitter of magnitude Dx in either the signal or reference arm of our interferometer will vary the phases, $\Psi_1$ and $\Psi_2$, by $k_1\Delta x$ and $k_2\Delta x$, respectively, with $k_1$ and $k_2$ the free space wavenumbers of the fundamental and second harmonic light beams. Since $k_2$ is exactly double $k_1$, the effect of jitter can be totally eliminated by subtracting twice $\Psi_1$ from $\Psi_2$. Note that such elimination is only possible when one wavelength is an integer multiple of the other. This operation yields, $\Delta L_{k_2,k_1}$, the difference in optical path lengths of the two wavelengths in the interferometer, with great sensitivity:

$$\Delta L_{k_2,k_1} = \frac{\Psi_2 - 2\Psi}{k_2}. \tag{1}$$

In the experiments presented below, the sensitivity achieved is about 5 nm in optical path length difference or, equivalently, about $9\times10^{-2}$ rad in phase difference with respect to the second harmonic light.

Figure 2:
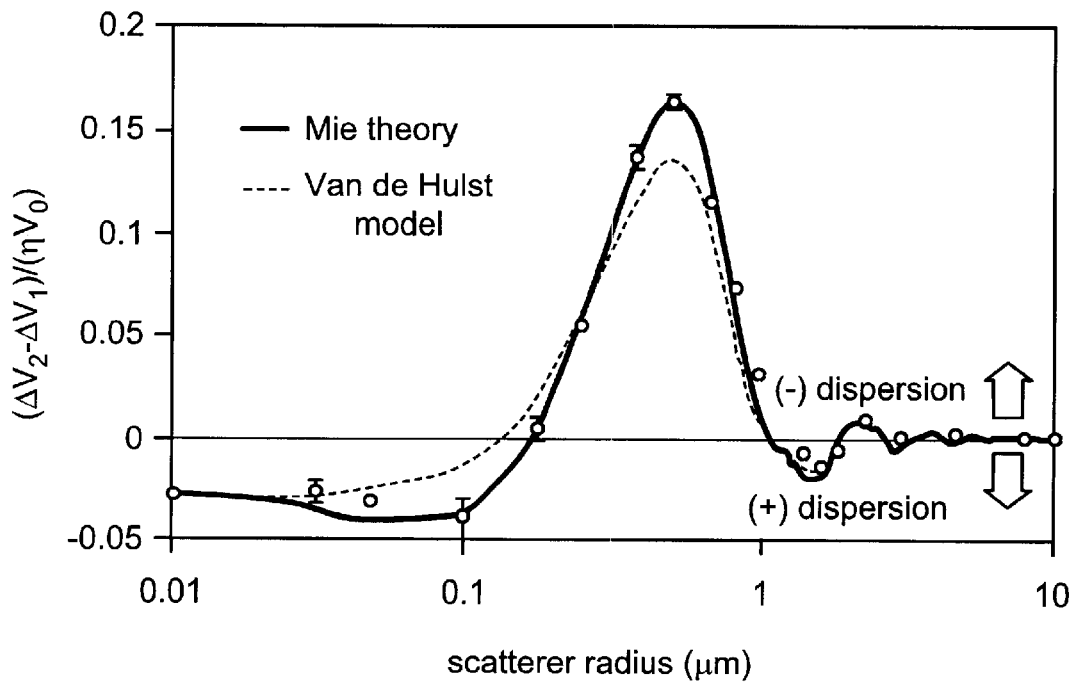
FIG. 2 illustrates phase velocity difference versus scatterer radius.

In a preferred embodiment, the phase of light traversing a 10 mm thick turbid medium composed of scattering polystyrene spheres in water can be measured. A water filled cuvette of the same thickness provides phase compensation. Note that because the ballistic light makes two trips through the cuvette, the effective thickness, L, is 20 mm. Polystyrene microspheres of a given size are gradually added to the signal arm cuvette, and the changes in optical path difference are measured. The fractional volume of microspheres, η, is varied from $8\times10^{-6}$ to $3\times10^{-3}$. The relative refractive index of the microspheres is 1.20 at 800 nm and 1.23 at 400 nm, with respect to that of water. Each measurement of optical path difference is then used to find the fractional phase velocity difference, $$\frac{\Delta v_2}{v_2} - \frac{\Delta v_1}{v_0},$$

between the two wavelengths in the cuvette:

$$\frac{\Delta v_2}{v_0} - \frac{\Delta v_1}{v_0} = -\frac{\Delta L_{k_2,k_1}}{n_0 L}, \tag{2}$$

with $v_0$ the speed of light in water and $n_0$ the refractive index of water. Note that second order corrections due to dispersion of water and turbidity are omitted, as they have minimal impact on the calculation. Our system can measure fractional changes in phase velocity difference as small as 2 parts in $10^7$. Measurements are made for a succession of microspheres varying in radius from 10 nm to 10 mm. The data points of FIG. 2 show the measured fractional difference in phase velocities as a function of scatterer size.

The transmission of the ballistic light through the turbid medium can be characterized by a complex index of refraction $n_{cx} = n - in'$. The ballistic light field, E(L), which has traversed a distance L in the turbid medium, can be written as a complex exponential attenuation of the incident field, E(0):

$$E(L) = E(0)e^{-ikn_{cx}L} = E(0)e^{-ikn(n-in')L}, \tag{3}$$

with k the wavenumber in the surrounding medium. The components of the refractive index can be expressed in terms of S(0), the scattering function evaluated in the exact forward direction of the input light:

$$n = 1 + \frac{2\pi N}{k^3}\text{Im}(S(O)), \tag{4a}$$

$$n' = \frac{2\pi N}{k^3}\text{Re}(S(O)), \tag{4b}$$

with N the number of scatterers per unit volume.

The imaginary part of the refractive index is associated with the well-known attenuation of ballistic light due to scattering and has been extensively studied. Note that, as determined by the optical theorem, attenuation occurs in the forward direction, even for non-absorbing particles. However, the effect of scatterers on the real part of the refractive index cannot be readily measured; to induce a change in n which is measurable by conventional methods requires such a large value of N that there is too little ballistic light to detect. The present interferometer allows us to circumvent this problem by providing a much more sensitive means of measurement. Thus, we can study subtle variations of the imaginary part of the scattering function.

To elucidate the effect of spherical scatterers on the refractive index (or, equivalently, the associated phase velocity), consider the van de Hulst scattering representation for spheres of radius a and refractive index m relative to the surrounding medium. In this representation, straight rays are traced through a spherical scatterer and assumed not to deviate during entry and exit. This is strictly valid only when the scatterer size is large compared to the wavelength and the refractive index difference is small. Nevertheless, it provides important physical insights and, as shown below, describes the salient features well beyond these limits. For light at one wavelength, the van de Hulst representation gives a fractional phase velocity change of the form:

$$\frac{\Delta v}{v_0} = 1 - n = -\frac{3\eta}{2a^3 k^3}(ka)^2\left(\frac{\sin\rho}{\rho^2} - \frac{\cos\rho}{\rho}\right), \quad (5)$$

with $\rho=2ka(m-1)$ the normalized scatterer size, and $(m-1)$ the relative refractive index difference between the scatterers and the surrounding medium. A plot of $$\frac{\Delta v}{\eta v_0}$$

using the van de Hulst representation is shown in FIG. 3. For comparison, an exact computation based on Mie theory is also shown.

FIG. 3 reveals three different regimes of ballistic light propagation, depending on the scatterer properties. Consider each of these analytically using the van de Hulst representation:

I. $\rho \ll 1$—Turbid Medium as Bulk Medium.
   In this limit, Eq. (5) reduces to:

$$\Delta v = -\eta v_0(m-1) \quad (6)$$

In this case, the change in phase velocity arises only from bulk refractive index change due to the presence of small scatterers. From another perspective, when the phase lag through each scatterer is small, the net result is simply an overall change in phase velocity, as determined by the refractive index difference.

II. $\rho \approx 1$—No Simplification.
   In this regime Eq. (5) cannot be simplified. The phase velocity is seen to oscillate with changing $\rho$. The net change in phase velocity is strongly dependent on whether the forward scattered light is in phase or out of phase with the input light. Note the existence of an anomalous phase velocity increase for some values of $\rho$, despite the fact that the scatterers have higher refractive index than water. In this situation, the effective refractive index of the medium is reduced by the addition of material with higher refractive index.

III. $\rho \gg 1$—phase velocity is independent of turbidity.
   In this limit, Eq. (5) reduces to:

$$\Delta v0 \quad (7)$$

The phase velocity is thus independent of the presence of turbidity. This is the only regime in which the photonic model provides a complete description. Physically, we can understand this from the fact that when $\rho$ is large, the phase of the transmitted light varies rapidly with increasing distance from the center of the sphere. The net result is that the phase shift of the transmitted light averages to zero.

The above is based on the behavior of ballistic propagation for light of a single wavelength. Based on phase velocity differences between two wavelengths, the three regimes still can be clearly seen (FIG. 2). The predicted phase velocity variation calculated from the van de Hulst representation, and the exact solution derived from Mie theory, are also shown in FIG. 2. The van de Hulst representation, though approximate, gives a good fit to the measured data.

The phase velocity difference of the two wavelengths reveals an additional phenomenon that is absent in single wavelength behavior, a dramatic region of negative dispersion (relative to water). Paradoxically, the negative dispersion is caused by the addition of appropriately sized positive dispersion scatterers. This effect is due to the shift in the phase velocity profile arising from the scaling of $\rho$ with wavelength. Note that it is not dependent on the anomalous phase velocity increase discussed above.

The distinctive features of the phase velocity difference profile makes it possible to extract precise scatterer size distributions in polydisperse media, by scanning the fundamental/second harmonic wavelengths. The high precision is afforded by the extremely high sensitivity achieved with phase-based measurements. This method complements related intensity-based techniques for measuring the size distribution of cell nuclei, an important indicator of precancerous changes in biological tissues. The phase dispersion measurement method described here can also form the basis of an imaging technique which is complementary to conventional phase contrast microscopy (PCM). In this case, image formation is based on the phase shift of ballistic light traversing the specimen. The use of ballistic light reveals a different type of information about the tissue compared to PCM, where the measured quantity is derived from scattered light. The present invention performs better than PCM in dispersive and weakly scattering tissues.

In this embodiment an interferometer 28 seen in FIG. 4, microscope objectives 03 and 04 focus the beam onto the sample such as excised tissue with a FWHM of about 7 $\mu$m at both wavelengths, however, there can be difficulty in aligning the returning path to overlap with the incoming path degrades the resolution to about 10 microns. A finer resolution can be achieved by using higher power objectives and improved alignment. The reference mirror moves at a constant velocity of 1 mm/s and induces a Doppler shift on the returning beam. As before, the two composite beams then are recombined, separated by their wavelength components with dichroic mirror, and measured separately by photodetectors.

To illustrate the sensitivity of this method, the refractive index dispersion change was measured by adding a small amount of DNA to water. The measurement is performed by replacing the microscope objectives (01 and 02), and the sample with a cuvette of very dilute herring testes DNA (0.014% vol. conc.). In this particular example, the cuvette is 10 mm thick, which makes L=20 mm due to the system's double pass configuration. The compensator 30 and its associated objectives (03 and 04) are correspondingly replaced by a cuvette containing only water. The measured refractive index dispersion, based on 10 separate measurements, is $(2.27\pm0.04)\times10^{-6}$.

Existing techniques provided a qualitative measurement resulting in an image where it is difficult to separate the contributions from absorption and phase shift. The present invention provides a quantitative measurement of the phase shift. In addition, existing techniques relied on small phase shifts between the scattered and unscattered light from the target for contrast, whereas the present invention directly measures the small phase shifts of the unscattered light associated with the refraction of the target. This results from the fact that interference-based techniques detect unscattered light far more efficiently than scattered light. Therefore, the present method can be applied to situations for which quantitative characterizations are required and where there is little or no scattering.

As an illustration, compare the performance of the method of prior phase contrast techniques to the method of the present invention on similarly prepares samples comprising a drop of water and a drop of DNA solution (1.0% vol. conc.) sandwiched between two cover slips. The separation between the cover slips is 170 $\mu$m. As evident in the lower image generated using a prior technique of FIG. 5, PDM can easily distinguish the two drops and provides a refractive index dispersion value for the DNA solution. In contrast, the upper image generated using a prior technique does not distinguish between the two. Interestingly, the refractive index dispersion measured in the experiment, $(1.3\pm0.2)\times10^{-4}$, differs from the value, $1.6\times10^{-4}$, extrapolated from the cuvette measurement, based only on the ratio of their concentrations. This difference can be attributed to the fact that the refractive index depends on scatterer size, as well as concentration. Thus, at higher concentration, the formation of DNA aggregater, which behave as scatterers, effectively alters the refractive index.

To further illustrate the present phase dispersion method to images of a brain tissue sample. A 16 $\mu$m thick sample was prepared from a frozen brain tissue block using a microtome. The sample was obtained from the autopsy material of an Alzheimer disease patient. A drop of glycerol was applied to keep the sample moist and to provide index matching. FIG. 6A shows phase contrast (top) and phase dispersion (middle) images taken from the same sample. For comparison, a stained sample from an adjacent thin section is also shown in the lower image. As can be seen, the phase contrast image reveals only a slight distinction between the gray and white matter, this is due to the relatively weak scattering of brain tissue. In comparison, the differences between the two are quite visible with the present method. This can be attributed to the biological differences in the composition of the two tissue types, which give rise to a small but measurable refractive index dispersion change.

Phase dispersion methods can also be used for 3D imaging, by employing a backscattering geometry. This provides tomographic phase dispersion images on in-vivo sites. This technique is very sensitive to small biological differences that manifest themselves as changes in the index of refraction. In addition, simultaneous measurement of the amplitude and phase of the heterodyne signals yields the real and imaginary parts of the refractive index, providing a more complete set of data about the scanned sample.

As seen in FIG. 6B, the upper left panel shows the structure to be imaged, the lower two panels show OCT images at 800 nm and 400 nm which fail to discriminate between gelatin and water. The upper right panel shows a differential phase image of the structure which in the lower band of the image clearly features the gelatin/water boundary after the light reflects off the mirror.

Thus, by spectrally scanning the fundamental/second harmonic wavelength, precise scatterer size distributions in tissue can be measured. The size characterization can far exceed the actual voxel resolution, as phase-based measurements are very sensitive to the spectral variation of the refractive index with scatterer size. This method complements related intensity-based techniques by rendering three dimensional images of the size distribution and chromatin content of cell nuclei which are important indicators of pre-cancerous or cancerous changes in biological tissues.

In a first embodiment both wavelengths need to be from low coherence sources. For example, a femtosecond Ti:sapphire laser source and its second harmonic generation. Another example, is two superluminescent diodes of appropriate wavelengths. In this manifestation, both wavelengths penetrate to the same scanned depth and are scattered/reflected back. Their relative phase is then measured after they interfere with their respective reference arm components to form heterodyne signals.

In another preferred embodiment illustrated in FIG. 7, is a 3D phase imaging system 50 in which only one wavelength needs to be from a low coherence source 52. The second wavelength may be form a coherent continuous wave 54 (CW) (or any other coherent source). The additional requirement is that the coherence length of the source is greater than the total length of the depth scan.

In this situation, the reflected component 64 of this light source, from the target's dominant reflecting/scattering surface 60, interferes with its reference arm component and generates a continuous heterodyne signal during depth wise scan of the target tissue 68. Its phase may then be used in a similar manner described above to eliminate jitter noises from the low coherence component of the pair of light sources. The low coherence component penetrates to the scanned depth and are reflected/scattered back. It forms a heterodyne signal with its reference arm component. In the embodiment in which two low coherence sources are used as described above in this imaging system, both wavelengths penetrate and are reflected and/or scattered by the tissue.

Illustrated in connection with FIG. 8 is a fiber optic system 200 for light delivery and/or collection in conjunction with the light scattering spectroscopic systems and methods of the invention described previously. A light source provides a beam 202 that includes at least two wavelengths $\lambda_1$, $\lambda_2$ which are coupled to the proximal end of optical fiber 204. A beam splitter 206 incorporated into the fiber optic system delivers light components through fibers 208 and 210, and through lenses 216 and 214, respectively. A first light component is reflected by moving mirror 220 traveling in direction 220, and returns through fibers 210 and 212. A second light component is directed onto tissue 218, and light scattered by the tissue is returned through fibers 208 and 212. Dichroic mirror 230 separates the two wavelength $\lambda_1$ and $\lambda_2$ which are detected by detectors 240 and 242, respectively. The heterodyne detection systems 250 and 252 are used to process the detected systems as described previously in connection with FIG. 1. The systems described herein can be used in conjunction with standard endoscopics to provide diagnostic information retrieved from lumens or tissue within the human body in vivo.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for optically measuring tissue comprising:
   providing a first wavelength and a second wavelength of light such that the second wavelength is harmonically related to the first wavelength;

directing light of the first wavelength and the second wavelength along both a first optical path and a second optical path, the first optical path extending onto the tissue to be measured and the second path undergoing a change in path length; and detecting light from the tissue and light from the second optical path to measure a change in phase of light interacting with the tissue.

2. The method of claim 1 wherein the tissue comprises human tissue.

3. The method of claim 1 further comprising determining a size of a particle within the medium.

4. The method of claim 1 further comprising forming an image of the medium with the detected scattered light.

5. The method of claim 1 further comprising measuring a change in phase velocity of light interacting with the medium.

6. The method of claim 1 further comprising providing light source that emits the first wavelength and a second wavelength that are harmonically related.

7. The method of claim 1 further comprising providing a first low coherence light source and a second low coherence light source.

8. The method of claim 1 further comprising providing a low coherence light source and a coherent light source.

9. The method of claim 1 wherein the second wavelength is within 5% of an integer multiple of the first wavelength.

10. The method of claim 1 further comprising providing a detector system connected to a data processor, the data processor determining characteristics of the tissue.

11. A method for optically measuring biological tissue comprising:

providing a first wavelength and a second wavelength of light such that the second wavelength is harmonically related to the first wavelength;

providing a detector system connected to a data processor;

directing light of the first wavelength and the second wavelength along both a first optical path and a second optical path, the first optical path extending onto the tissue to be measured and the second path undergoing a change in path length;

detecting light from the tissue and light from the second optical path with the detector system to measure a change in phase of light interacting with the tissue; and determining a characteristic of the tissue with the data processor using the measured change in phase.

12. The method of claim 11 further comprising determining a size of a particle within the medium.

13. The method of claim 11 further comprising forming an image of the medium with the detected scattered light.

14. The method of claim 11 further comprising measuring a change in phase velocity of light interacting with the medium.

15. The method of claim 11 further comprising providing light source that emits the first wavelength and a second wavelength that are harmonically related.

16. The method of claim 11 further comprising providing a first low coherence light source and a second low coherence light source.

17. The method of claim 11 further comprising providing a low coherence light source and a coherent light source.

18. The method of claim 11 wherein the second wavelength is within 5% of an integer multiple of the first wavelength.

19. The method of claim 11 further comprising providing a compensator and a scanning mirror along the second optical path.

20. The method of claim 11 wherein the step of providing a detector system comprises providing a first detector that detects the first wavelength and a second detector that measures the second wavelength.

21. The method of claim 11 further comprising coupling light from a light source to the tissue with a fiber optic device.

22. A device for optically measuring a medium comprising:

a light source that provides a first wavelength and a second wavelength of light such that the second wavelength harmonically related to the first wavelength;

an optical system that couples light of the first wavelength and the second wavelength along both a first optical path and a second optical path, the first optical path extending onto a medium to be measured and the second path undergoing a change in path length; and a detector that detects light from the medium and light from the second optical path to measure a change in phase of light interacting with the medium.

23. The device of claim 22 wherein the medium comprises biological tissue.

24. The device of claim 22 further comprising a data processor that determines a size of a particle within the medium.

25. The device of claim 22 further comprising a data processor that forms an image of the medium with the detected scattered light.

26. The device of claim 22 further comprising a data processor that determines a change in phase velocity of light interacting with the medium.

27. The device of claim 22 wherein the light source emits light in the visible and near-infrared regions.

28. The device of claim 22 further comprising providing a first low coherence light source and a second low coherence light source.

29. The device of claim 22 further comprising providing a low coherence light source and a coherent light source.

30. The device of claim 22 wherein the second wavelength is within 5% of an integer multiple of the first wavelength.

31. The device of claim 22 further comprising a fiber optic device that couples light from the light source on the medium.

32. The device of claim 22 further comprising a fiber optic device that couples light from the medium to the detector.

33. The device of claim 22 wherein the detector comprises a first photodetector and a second photodetector.

34. The device of claim 22 further comprising a compensator.

35. The device of claim 22 further comprising a first scanning mirror reflecting light on the first optical path and a second mirror reflecting light on the second optical path.

36. The device of claim 22 further comprising a beam splitter and a plurality of lenses.

37. The device of claim 22 further comprising an analog to digital converter connected to the detector.

38. The device of claim 22 further comprising a heterodyne detection system.

39. The device of claim 22 further comprising a fiber optic probe and an endoscope.

40. The device of claim 22 wherein the light source comprises a continuous wave laser.

* * * * *